United States Patent [19]

DePetrillo

[11] Patent Number: 6,144,877

[45] Date of Patent: Nov. 7, 2000

[54] DETERMINING THE HURST EXPONENT FOR TIME SERIES DATA

[75] Inventor: Paolo B. DePetrillo, Bethesda, Md.

[73] Assignee: The United States of America as represented by the Department of Health and Human Services, Washington, D.C.

[21] Appl. No.: 09/132,462

[22] Filed: Aug. 11, 1998

[51] Int. Cl.[7] .................................. A61B 5/00; A61B 5/04
[52] U.S. Cl. ............................................................. 600/515
[58] Field of Search ............................................. 600/515

[56] References Cited

U.S. PATENT DOCUMENTS

| | | |
|---|---|---|
| 4,960,129 | 10/1990 | dePaola et al. . |
| 5,213,106 | 5/1993 | Lerner . |
| 5,299,119 | 3/1994 | Kraf et al. . |
| 5,623,925 | 4/1997 | Swenson et al. . |
| 5,678,561 | 10/1997 | Karagueuzian et al. . |
| 5,682,901 | 11/1997 | Kamen . |
| 5,732,158 | 3/1998 | Jaenisch . |

OTHER PUBLICATIONS

"The Value of Cardiovascular Autonomic Function Tests: 10 Years Experience in Diabetes," David J. Ewing et al., *Diabetes Care*, vol. 8, No. 5, pp. 491–498, Sep.–Oct. 1985.

"Heart Rate—Respiration Relationship: Computerized Method For Early Assessment Of Cardiac Autonomic Damage In Diabetic Patients," L. Bernardi et al., *Acta Cardiologica*, vol. XLI, No. 3, pp. 197–206, 1986.

"Somatic and Autonomic Function in Progressive Autonomic Failure and Multiple System Atrophy," Jeffrey Cohen et al., *Annals of Neurology*, vol. 22, No. 6, pp. 692–699, Dec. 1987.

"Autonomic neuropathy in an alcoholic population," Fiona Barter et al., *Postgraduate Medical Journal*, vol. 63, pp. 1033–1036, 1987.

"Autonomic Neuropathy In AIDS," R.F. Miller et al., *The Lancet*, pp. 343–344, Aug. 8, 1987.

"Autonomic Neuropathy and HIV Infection," Antonio Villa et al., *The Lancet*, p. 915, Oct. 17, 1987.

"Sensitivity of R–R Variation and Valsalva Ratio in Assessment of Cardiovascular Diabetic Autonomic Neuropathy," Armand H. Rothschild et al., *Diabetes Care*, vol. 10, No. 6, pp. 735–741, Nov.–Dec. 1987.

"Heart rate variability: A measure of cardiac autonomic tone," Phyllis K. Stein et al., *Am. Heart J.*, 127:1376–81, 1994.

"On the fractal nature of heart rate variability in humans: effects of data length and $\beta$–adrenergic blockade," Yoshiharu Yamamoto et al., *Am. J. Physiol.*, 266:R40–R49, 1994.

"Autonomic neurotoxicity of alcohol assessed by heart rate variability," Katsuyuji Murata et al., *Journal of the Autonomic Nervous System*, vol. 48, pp. 105–111, 1994.

"On the fractal nature of heart rate variability in humans: effects of vagal blockade," Yoshiharu Yamamoto et al., *Am. J. Physiol.*, 269:R830–R837, 1995.

"Fractal Mechanisms and Heart Rate Dynamics," C–K. Peng et al., *Journal of Electrocardiology*, vol. 28 Supplement, pp. 59–65, 1995.

(List continued on next page.)

*Primary Examiner*—Carl H. Layno
*Attorney, Agent, or Firm*—Venable; Michael A. Sartori

[57] ABSTRACT

Statistical information is determined for time series data of a measurable activity. The time series data of the measurable activity is obtained and comprises data elements representative of the measurable activity. A Hurst exponent is determined from the time series data and is the statistical information of the time series data.

45 Claims, 5 Drawing Sheets

OTHER PUBLICATIONS

"Estrogen Control of Central Neurotransmission: Effect on Mood, Mental State, and Memory," George Fink et al., *Cellular and Molecular Neurobiology*, vol. 16, No. 3, pp. 325–336, 1996.

"Cardiovascular Variability in Major Depressive Disorder and Effects of Imipramine or Mirtazapine (Org 3770)," *Journal of Clinical Psychopharmacology*, vol. 16, No. 2, pp. 135–145, 1996.

"Experimental human endotoxemia increases cardiac regularity: Results from a prospective, randomized, crossover trial," Paul J. Godin et al., *Crit Care Med*, vol. 24, No. 7., pp. 1117–1124, 1996.

"Fish Consumption, n–3 Fatty Acids in Cell Membranes, and Heart Rate Variability in Survivors of Myocardial Infarction With Left Ventricular Dysfunction," Jeppe Hagstrup Christensen et al., *The American Journal Of Cardiology*, vol. 79, pp. 1670–1673, Jun. 15, 1997.

"Dynamic Analysis of Heart Rate May Predict Subsequent Ventricular Tachycardia After Myocardial Infarction," Timo H. Mäkikallio et al., *The American Journal Of Cardiology*, vol. 80, pp. 779–783, Sep. 15, 1997.

"Decrease of cardiac chaos in congestive heart failure," Chi–Sang Poon et al., *Nature*, vol. 389/2, pp. 492–495, Oct. 1997.

"Decomplexification in critical illness and injury: Relationship between heart rate variability, severity of illness, and outcome," Brahm Goldstein, *Crit Care Med*, vol. 26, No. 2, pp. 352–357, 1998.

"Heart rate variability—A potential, noninvasive prognostic index in the critically ill patient," Harold L. Kennedy, *Crit Care Med*, vol. 26, No. 2, pp. 213–214, 1998.

DETERMINING THE HURST EXPONENT FOR TIME SERIES DATA

FIELD OF THE INVENTION

The invention relates to a method, an apparatus, and a computer-readable medium for determining statistical information for time series data and for detecting a biological condition of a biological system from the statistical information.

REFERENCES

For the convenience of the reader, the publications referred to in the specification are listed below. In the specification, a numeral within parentheses refers to the respective numbered publication, except for those which clearly refer to equations. The listed publications are incorporated herein by reference.

1. Barnsley, M. F. et al., "The Science of Fractal Images," Springer-Verlag, New York, 1988.
2. Bassingthwaighte, J. B. et al., "Evaluation of the dispersional analysis method for fractal time series," Ann. Biomed. Eng., 23:491–505, 1995.
3. Feder, J., "Fractals," New York, Plenum Press, 1988.
4. Fischer, R. et al., "A comparison of analytical methods for the study of fractional brownian motion," Ann. Biomed. Eng., 24:537–543, 1996.
5. Mandelbrot, B. B. et al., "Fractional Brownian motions, fractional noises and applications," SIAM Review, 10:422–437, 1968.
6. Peng, C. K. et al., "Non-equilibrium dynamics as an indispensable characteristic of a healthy biological system," Integr. Physiol. Behav. Sci., 29:283–293, 1994.
7. Stein, P. K. et al., "Heart rate variability: A measure of cardiac autonomic tone," Am. Heart. J., 127:1376–1381, 1994.
8. Voss, R. F., "Random fractals: Characterization and measurement," in Scaling Phenomena in Disordered Systems, edited by Pynn, R. et al., Plenum Press, New York, 1985.
9. Yamamoto Y. et al., "On the fractal nature of heart rate variability in humans: Effects of data length and $\beta$-adrenergic blockade," Am. J. Physiol. 266:R40–R49, 1994.
10. Yamamoto, Y. et al., "Effects of acute exposure to simulated altitude on heart rate variability during exercise," J. Appl. Physiol. 81:1223–1229, 1996.
11. Miralles, R. et al., "Autonomic neuropathy in chronic alcoholism: Evaluation of cardiovascular, pupillary, and sympathetic skin responses," Eur. Neurol. 35:287–292, 1995.
12. Hirsch, J. A. et al., "Recovery of respiratory sinus arrhythmia in detoxified alcoholic subjects," J. Appl. Physiol. 74:1816–1823, 1993.
13. Hurst, H. E., "Long-term storage capacity of reservoirs," Trans. Amer. Soc. Civ. Engrs. 116:770–808, 1951.
14. Peng, C. K. et al., "Fractal mechanisms and heart rate dynamics," Journal of Electrocardiology, 28 Suppl. 59–65, 1995.
15. Yamamoto, Y. et al., "On the fractal nature of heart rate variability in humans: Effects of vagal blockade," Am. J. Physiol. 269:R830–R837, 1995.
16. Murata, K. et al., "Autonomic neurotoxicity of alcohol assessed by heart rate variability," J. Autonomic Nervous System 48:105–111, 1994.
17. Spitzer, R. L. et al., "Structured Clinical Interview for DSM-III-r-Non-Patient Edition" (SCID-NP, Version 1.0), Washington, D.C., American Psychiatric Press, 1990.
18. Barnsley, M. F. et al., "The Science of Fractal Images," New York, Springer-Verlag, 1988.
19. Convertino, V. A. et al., "Effects of vestibular and oculomotor stimulation on responsiveness of the carotid-cardiac reflex," Am. J. Physiol. 42:R615–R622, 1997.
20. Ryan, S. M. et al., "Gender and age-related differences in heart rate dynamics: Are women more complex than men?", JACC 24:1700–1707, 1994.
21. Bailey, J. et al., "Effects of constant cardiac autonomic nerve stimulation on heart rate variability," Am. J. Phys. 270:H2081–H2087, 1996.
22. Sevoz, C. et al., "Role of serotonin3 receptors in the nucleus tactus solitarii on the carotid chemoreflex," Am. J. Phys. 272:H1250–1259, 1997.
23. Yamano, M. et al., "Species difference in the 5-hydroxytryptamine receptor associated with the von Bezold-Jarsich reflex," Arch. Int. Pharmacodyn. 330:177–189, 1995.
24. Yoshimoto, K., "Possibility of 5-HT3 receptor involvement in alcohol dependence: A microdialysis study of nucleus accumbens dopamine and serotonin release in rats with chronic alcohol consumption," Alcohol. Clin. Exp. Res. 20 (Suppl.):311A–319A, 1996.
25. Virkkunen, M. et al., "Serotonin in early-onset alcoholism," Recent Dev. Alcohol. 13:173–89, 1997.
26. Krystal, J. H. et al., "Serotonergic and noradrenergic dysregulation in alcoholism: m-chlorophenylpiperazine and yohimbine effects in recently detoxified alcoholics and healthy comparison subjects," Am. J. Psychiatry 153:83–92, 1996.
27. Fink, G. et al., "Estrogen control of central neurotransmission: Effect on mood, mental state, and memory," Cell. Mol. Neurobiol. 16:325–44, 1996.
28. Lippert, T. H. et al., "Serotonin metabolite excretion after postmenopausal estradiol therapy," Maturitas 24:37–41, 1996.
29. Tucker, P. et al., "Paroxetine increases heart rate variability," Journal of Clinical Psychopharmacology 17:370–376, 1997.
30. Johnson, R. H. et al., "Mortality in alcoholics with autonomic neuropathy," Neurol. Neurosurg. Psychiatry 51:476–480, 1988.
31. Urbano-Marwquez, A. et al., "The effects of alcoholism on skeletal and cardiac muscle," NEJM 320:409–415, 1989.
32. Butler, G. C. et al., "Fractal component of variability of heart rate and systolic pressure in congestive heart failure," Clinical Science 92:543–550, 1993.
33. Makikallio, T. H. et al., "Dynamic analysis of heart rate may predict subsequent ventricular tachycardia after myocardial infarction," Am. J. Cardiology 80:779–782, 1997.
34. Rich, M. W. et al., "Correlation of heart rate variability with clinical and angiographic variables and late mortality after coronary angiography," Am. J. Cardiol. 62:714–717, 1988.
35. Yeragani, V. K. et al., "Depression and heart rate variability," Biol. Psychiatry, 38(11):768–770, 1995.
36. Mezzacappa, E. et al., "Antisocial behavior, and heart rate regulation in adolescent males," J. Child Psychol. Psychiatry, 38(4):457–469, 1997.

37. Cohen, H. et al., "Power spectral analysis of heart rate variability in posttraumatic stress disorder patients," Biol. Psychiatry, 41(5):627–629, 1997.

38. Thayer, J. F. et al., "Autonomic characteristics of generalized anxiety disorder and worry," Biol. Psychiatry, 39(4):255–266, 1996.

39. Voss, A. et al., "Multiparametric analysis of heart rate variability used for risk stratification among survivors of acute myocardial infarction," Pacing Clin. Electrophysiol., 21(1 Pt. 2):186–192, 1998.

40. Bikkina, M. et al., "Diminished short-term heart rate variability predicts inducible ventricular tachycardia," Chest., 113(2):312–316, 1998.

41. Dabrowski, A. et al., "Low variability of cycle lengths in nonsustained ventricular tachycardia as an independent predictor of mortality after myocardial infarction," Am. J. Cardiol., 80(10):1347–1350, 1997.

42. Makikallio, T. H. et al., "Dynamic analysis of heart rate may predict subsequent ventricular tachycardia after myocardial infraction," Am. J. Cardiol., 80(6):779–783, 1997.

43. Carney, R. M. et al., "Association of depression with reduced heart rate variability in coronary artery disease," Am. J. Cardiol., 76(8):562–564, 1995.

44. Tulen, J. H. et al., "Cardiovascular variability in major depressive disorder and effects of imipramine or mirtazapine (Org. 3770)," J. Clin. Psychopharmacol., 16(2):135–145, 1996.

BACKGROUND OF THE INVENTION

Measures of heart rate variability (HRV) have been shown to be a powerful means of assessing the influences of autonomic tone on cardiac function (8). However, because some methodological problems exist in obtaining reliable estimates of this measure, the practical application of HRV is limited, and the interpretation of such results is confounded. For example, in time domain analysis, measures of dispersion, such as the standard deviation, increase with increasing data length, making cross-study comparisons difficult. Further, dispersion measures also do not take into account the degree of temporal autocorrelation.

Conventionally, problems due to autocorrelations can be avoided by conducting the analysis in the frequency domain using a fast Fourier transform. However, this method assumes that for the epoch investigated, the time series remains stationary. This assumption is less likely to hold true as longer time intervals are sampled. On the other hand, short data lengths are also problematic because the contributions of low frequencies to the overall power spectrum cannot properly be estimated. Consequently, the outcomes of applying time domain analysis or frequency domain analysis are not easily interpreted when the recording time of the HRV is relatively short, such as less than five minutes, or when the length of the recorded time series varies significantly between individuals. Previous work suggests a strong correlation between alcohol dependence and altered heart rate dynamics. Heart rate dynamics are usually estimated using parameters obtained from time-domain or frequency-domain analyses (11, 12). Results obtained with these methods are confounded by the changing statistical properties of heartbeat interval time series over time, called non-stationary signals. These signals are difficult to interpret with dispersional measures in the time-domain, such as the standard deviation, because the results are not stable with increasing data length. These measures also provide no information regarding the internal dynamics of the time series. Frequency-domain measures rely on assumptions of stationarity that are not met with interbeat interval (IBI) time series data, especially with longer recording times.

SUMMARY OF THE INVENTION

It is an object of the invention to determine the Hurst exponent from time series data.

It is another object of the invention to detect a biological condition of a biological subject by determining the Hurst exponent from time series data measured from the biological subject.

It is a further object of the invention to determine the Hurst exponent for an IBI time series from a human subject.

It is still another object of the invention to determine the Hurst exponent from a small number of data points in a time series.

The above objects and advantages of the present invention are achieved by a method, an apparatus, and an article of manufacture for determining the Hurst exponent for time series data.

The method of the invention includes a method for determining statistical information for time series data for a measurable activity, the method comprising the steps of: obtaining the time series data of the measurable activity, the time series data comprising a plurality of data elements representative of the measurable activity; and determining a Hurst exponent from the time series data, the Hurst exponent being the statistical information of the time series data.

The apparatus of the invention includes an apparatus for determining statistical information for time series data for a measurable activity, comprising: means for obtaining the time series data of the measurable activity, the time series data comprising a plurality of data elements representative of the measurable activity; and means for determining a Hurst exponent from the time series data, the Hurst exponent being the statistical information of the time series data.

The article of manufacture of the invention includes a computer-readable medium embodying code segments for determining statistical information for time series data for a measurable activity, comprising: code segments for obtaining the time series data of the measurable activity, the time series data comprising a plurality of data elements representative of the measurable activity; and code segments for determining a Hurst exponent from the time series data, the Hurst exponent being the statistical information of the time series data.

The apparatus of the invention includes a computer programmed with software to operate the computer in accordance with the invention. Examples of "computer" include: a general purpose computer; an interactive television; a hybrid combination of a general purpose computer and an interactive television; and any apparatus comprising a processor, memory, the capability to receive input, and the capability to generate output.

The article of manufacture of the invention comprises a computer-readable medium embodying code segments to control a computer to perform the invention. Examples of a "computer-readable medium" include: a magnetic hard disk; a floppy disk; an optical disk, such as a CD-ROM or one using the DVD standard; a magnetic tape; a memory chip; a carrier wave used to carry computer-readable electronic data, such as those used in transmitting and receiving electronic mail or in accessing a network, such as the Internet or a local area network ("LAN"); and any storage device used for storing data accessible by a computer. Further, examples of "code segments" include: software; instructions; computer programs; or any means for controlling a computer.

Moreover, the above objects and advantages of the invention are illustrative, and not exhaustive, of those which can be achieved by the invention. Thus, these and other objects and advantages of the invention will be apparent from the description herein or can be learned from practicing the invention, both as embodied here and as modified in view of any variations which may be apparent to those skilled in the art.

BRIEF DESCRIPTION OF THE DRAWINGS

Embodiments of the invention are explained in greater detail by way of the drawings.

DETAILED DESCRIPTION OF THE INVENTION

The Hurst exponent H is a measure of the dynamics of a time series, as conceived by Hurst (3) and formalized by Mandelbrot (4). In particular, H is a measure of the persistence, or anti-persistence, of trends within serial measurements. The value of H varies between 0 and 1, namely $0 \leq H \leq 1$. As H approaches 1, increasing or decreasing trends in consecutive data points in a time series are reinforced, and the time series is said to be persistent. Consequently, a time series having an H value close to 1 shows relatively little variation between consecutive data samples. Conversely, as H approaches 0, positive and negative trends alternate rapidly, and the time series is said to be anti-persistent. In this extreme, the absolute differences in values between consecutive time points of the time series tend to be large. A time series of the increments between adjacent values tends to show a linear relationship between the power spectrum and frequency as H approaches 0. As H approaches the value of 0.5, the correlation between consecutive elements of the time series vanishes, displaying the characteristics of (one-dimensional) Brownian motion. Mandelbrot (5) formally related H to fractional Brownian motion, which made the Hurst exponent available as a descriptor of the scaling behavior of fractal curves, called self-similarity.

Figure 1:
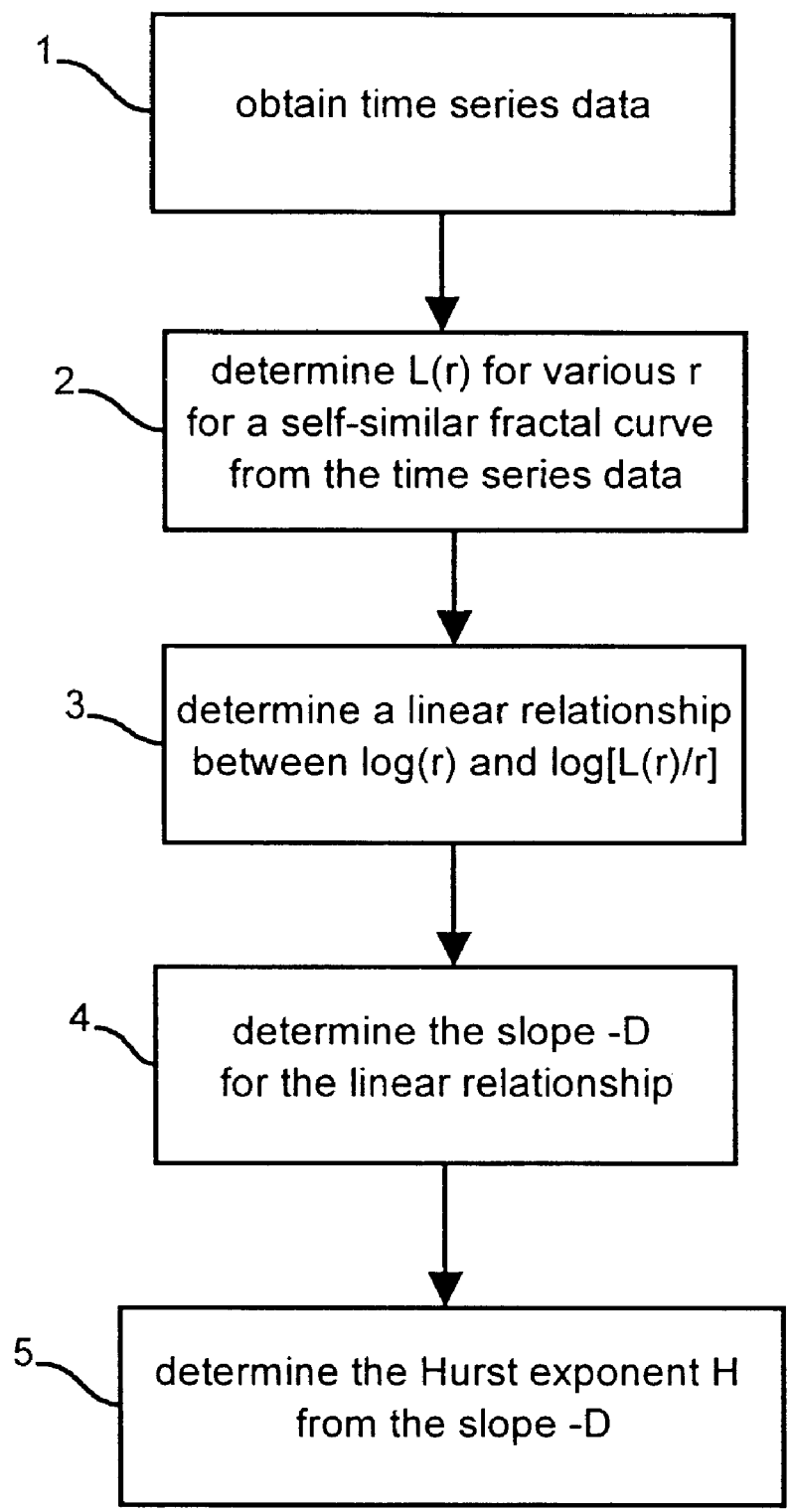
FIG. 1 illustrates a flow diagram for the invention.

FIG. 1 illustrates a flow diagram for the invention. In block 1, time series data is obtained. For example, the time series data can be obtained from measuring a measurable activity, such as measuring the heartbeat of a biological subject. The biological subject can be, for example, a human subject. The time series can also be obtained by retrieving the time series data from a computer-readable medium. Another example of a time series is an IBI time series, which can be extracted from a heartbeat time series.

In block 2, using the time series data, the lengths L(r) for a number of self-similar fractal curves are determined for various values of r up to a maximum value of M and for an embedding dimension n. The length of a self-similar fractal curve is given by the following relationship (9):

$$L(r) = (L_{max}) r^{(1-D)} \qquad (1)$$

where the length L(r) is measured as the Euclidean distance between sampled values of the time series, r is the sampling resolution or "yardstick size" and is an integer greater than 0 (i.e., r>0), and D is the similarity dimension and $0 \leq D \leq 2$. When r=1, L is computed using every sample value of the time series and reaches a maximum length $L_{max}$. For r=2, every second sample is used in the length computation, and $L < L_{max}$ because "peaks" and "valleys" of width <2 do not contribute to the total length. With increasing values of r, progressively wider local maxima and local minima are disregarded and, if the curve is self-similar, the total length decreases according to equation (1).

Before the time series can be scaled, the time series must be embedded in n-dimensional space as an n-dimensional curve. For an embedding dimension of n, the coordinates of each point within the so-called phase-space are determined by the values of the n consecutive samples of the time series. When n=3, each sample of the time series is represented in three-dimensional space as a point $P=(x,y,z)=(S_i, S_{i+1}, S_{i+2})$. The x-axis represents the sample $S_i$ of the time series $T(S_1, S_2, S_3, \ldots, S_i, \ldots, S_N)$, and the y-axis and z-axis represent the magnitude of the phase advanced elements of the time series, namely, time+1 and time+2, respectively.

Figure 3:
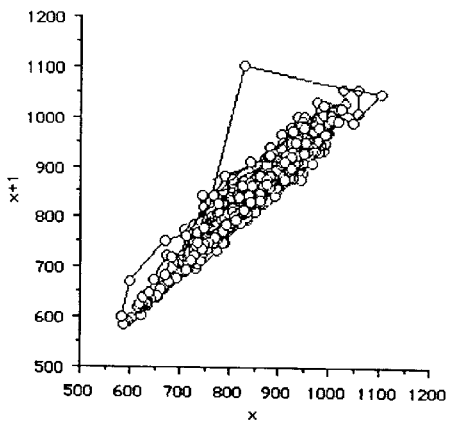
FIG. 3 illustrates a phase-space plot for an IBI of a human subject.

FIG. 3 illustrates a phase-space plot for n=2 of an IBI time series of 1000 data points taken from a healthy human subject during mild exertion, namely, walking. The coordinates on the x-axis represent the original time series in milliseconds. The coordinates on the y-axis represent the phase-advanced value of the time series, also in milliseconds. Consecutive points are connected by a straight line.

Scaling of the time series is accomplished by computing the sum of the lengths of all vectors in n-space that connect each succeeding point on the n-dimensional curve. For any embedding dimension, the geometric length L of the curve can be determined for any sampling resolution r as L(r). When r=1, L(r) is calculated by the summation of the geometric length of the curve joining every point in phase-space. When r=2, L(r) is calculated by summing the geometric length of the curve joining every other point in phase space. This process is continued for increasing values of r to yield a relationship between L(r) and r. For succeeding computations with different r, a new curve is generated, connecting points along the original curve, but sampled at a lower resolution.

In general, the relationship between the length L(r) and the sampling resolution r is given by:

$$L(r) = \sum_{i=0}^{I} \left[ \sum_{k=0}^{n-1} (S_{ir+k} - S_{ir+r+k})^2 \right]^{1/2} \qquad (2)$$

where the time series data is represented by $S_1, S_2, S_3, \ldots, S_N$, $r=1,2,3,\ldots,M$, I is the integer part of (N-r-n+1)/r, $n \geq 1$ is an embedding dimension, N is the number of data points of the time series vector $T(S_1, S_2, S_3, \ldots, S_i, \ldots, S_N)$ and M is the maximum number of scales. Thus, in block 2, for an embedding dimension of n, equation (2) can be used to determine L(r) for various r for a times series of N data points.

For the embedding dimension of n=3, the value of L(r) for the three-dimensional phase-space is given by:

$$L(r) = \sum_{i=0}^{I} \sqrt{(S_{ir} - S_{ir+r})^2 + (S_{ir+1} - S_{ir+r+1})^2 + (S_{ir+2} - S_{ir+r+2})^2} \quad (3)$$

where the time series data is represented by $S_1, S_2, S_3, \ldots, S_N$, $r=1,2,3,\ldots,M$, and I is the integer part of (N-r-n+1)/r.

For equations (2) and (3), the choice of M should be dictated by the length of the time series. The inventor has discovered that the relationship between log (r) and log [L(r)/r] remains relatively linear when $M<(N)^{1/2}$. If the M is set too high, some deviation from linearity will occur at higher values of r in the relationship, which will bias the results.

Since each point in the phase-space contains information with respect to adjacent elements of the time series, the choice of the embedding dimension depends on the dynamics of the time series. In general, the best choice of the embedding dimension corresponds to the largest number of elements which encompass the "memory" of the time series. For a true fractional Brownian process, this is known to be infinite (5). However, for a particular physiological system, the memory of the process appears to degrade rapidly, so that the appropriate embedding dimension n can be experimentally determined by testing for convergence of the slope of the log—log plot of r vs. L(r)/r. Choosing higher embedding dimensions than is required by the dynamics of the time series exponentially increases computing time, while not significantly altering the final value of D, and therefore H.

In block 3, a linear relationship between log (r) and log [L(r)/r] is determined. The log transformation of equation (1) yields:

$$\log [L(r)/r] = \log (L_{max}) - D[\log (r)] \quad (4)$$

where r>0. Equation (4) has the form of a linear equation with y-axis intercept log ($L_{max}$) and a slope of -D. Hence, if the time series exhibits self-similar scaling behavior, a plot of log (r) vs. log [L(r)/r] will result in a straight line with a y-axis intercept of log ($L_{max}$) and a slope of -D. To determine the linear relationship in equation (4), a linear regression with a least mean squares fit of the log (r) vs. log [L(r)/r] plot can be performed.

In block 4, the slope -D of the linear relationship from block 3 is determined.

In block 5, the Hurst exponent H is determined from the slope -D of block 4. The similarity dimension D of the curve is related to H by the following equation:

$$H = 2 - D. \quad (5)$$

Figure 9:
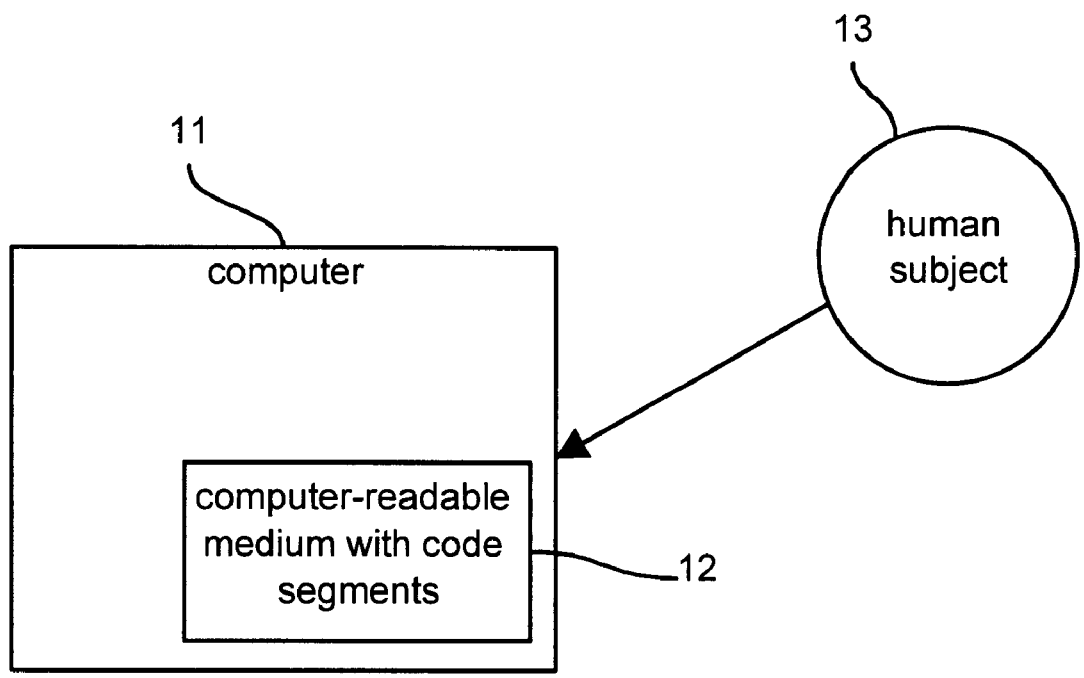
FIG. 9 illustrates an apparatus and an article of manufacture for implementing the invention.

FIG. 9 illustrates an apparatus and an article of manufacture for implementing the invention. As discussed above, the computer in accordance with the invention includes a computer 11 programmed with software to operate the computer in accordance with the invention, an embodiment of which is depicted in the flow diagram of FIG. 1. Further, the article of manufacture of the invention includes a computer-readable medium 12 embodying code segments to control the computer 11 to perform the invention, an embodiment of which is depicted in the flow diagram of FIG. 1. In addition, FIG. 9 illustrates the computer 11 for obtaining time series data from a human subject 13 and for obtaining time series data by retrieving the time series data from the computer-readable medium 12.

TESTING THE INVENTION

Figure 2:
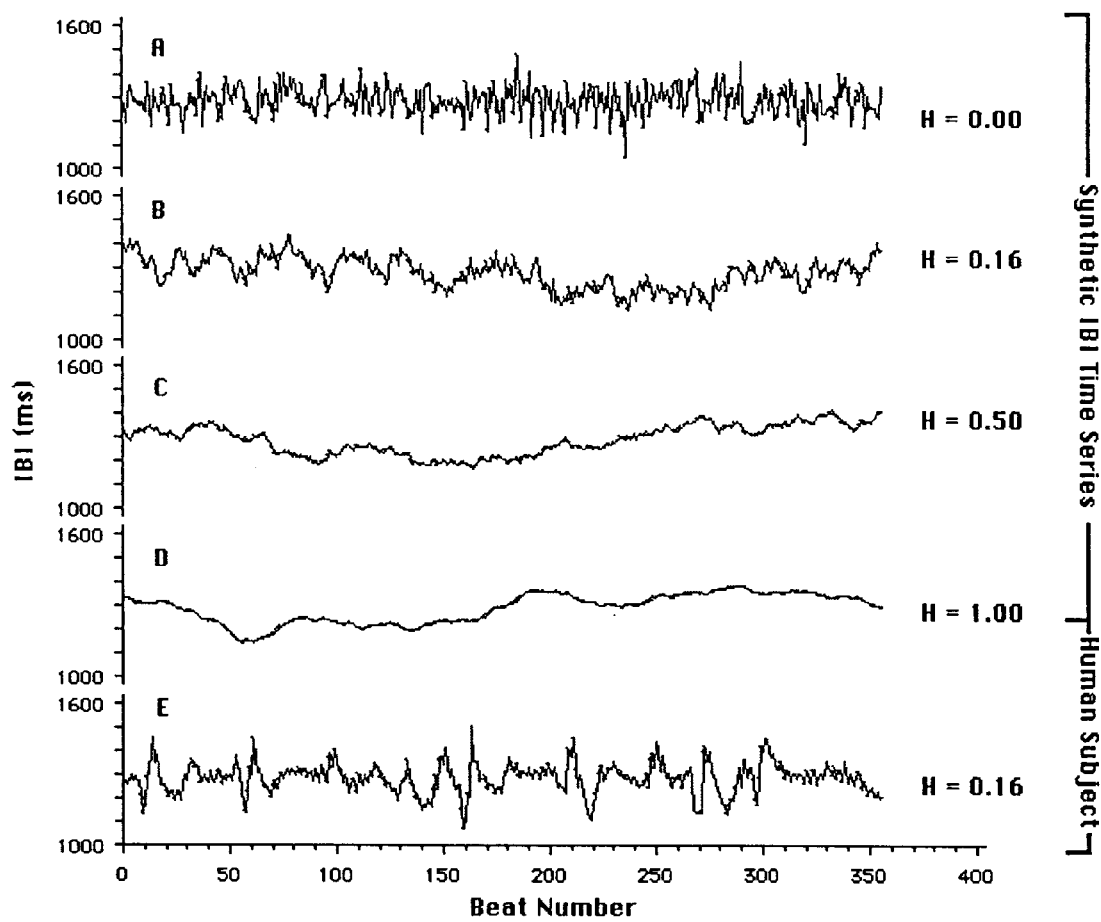
FIG. 2 illustrates five time series data for various values of the Hurst experiment.

FIG. 2 illustrates five cardiac IBI time series for various Hurst exponents. The y-axes represent the IBI time in milliseconds (ms), and the x-axis represents the beat number. The time series A to D were synthesized and correspond to the H value shown on the right hand side of the figure. The time series E was taken from data from a human subject, and the H value was derived using the invention.

The synthetic IBI time series A to D shown in FIG. 1 were computed using a spectral synthesis method (19) from the Time-Series Statistical Analysis System TSAS 3.01.01b, written by Yoshiharu Yamamoto, Ph.D., Lab. For Exercise Physiol. & Biomechanics, Grad. School of Education, The University of Tokyo, 7-3-1 Hongo, Bunkyo-ku, Tokyo 113, Japan, and were compiled and run on a DEC 3000/600S AXP (Digital Equipment Corp., Maynard, Mass.) This module conveniently allows varying the length, mean, standard deviation, and spectral characteristics of the resulting time series using the spectral synthesis method.

Inspecting time series D with H=1.0 in FIG. 1, an overall relative smoothness can be seen. As H approaches 0, trends are more rapidly reversed, as shown in time series A, where large variations occur between adjacent values, which give the time series A an irregular look. When H=0.5, as shown in time series C, the magnitudes of the sequential points of the time series are independent and uncorrelated, and time series C can be considered a random walk. Thus, H values approaching 0.5 from either extreme are symptomatic of a breakdown in the long-range correlations of the IBI time series.

The four time series A to D illustrated in FIG. 2 were generated to have the same mean and standard deviation as the IBI time series obtained from the healthy human subject, illustrated in time series E. In particular, the mean and standard devication are 1286.97±63.19 ms. As shown in time series E, the time series from the healthy human subject had an associated H value of 0.16±-0.05. By visual inspection, the "roughness" of time series E best matches the synthesized IBI series from time series B with H=0.16.

The invention was tested using electrocardiogram (EKG) data from nine healthy human subjects. Results for the calculation of H derived from equation (5) are shown in Table 1. In Table 1, the first column lists the subject identification number, the second column lists the determined H and its standard error (H±SEM), the third column lists the maximum value of the scale (M), the fourth column lists the square of the correlation coefficient ($R^2$), and the fifth column lists the mean of the IBI and its standard deviation in milliseconds (mean±SD). In Table 1, subject 4 was engaged in moderately heavy exercise, while subject 5 was examined during very heavy exercise (entry 5a), and at rest (entry 5b). The values of H obtained for resting subjects 1, 2, 3, 5a, 7, and 8 are consistent with values of H obtained by coarse-graining spectral analysis (CGSA) (9). The higher value of H seen in subject 5b is consistent with increased H values obtained during exercise (10).

TABLE 1

Results of Analysis of Human Subject EKGs

| Subject ID | H ± SEM | M | R² | mean ± SD |
|---|---|---|---|---|
| 1 | 0.07 ± 0.02 | 31 | 0.998 | 1034.33 ± 91.32 |
| 2 | 0.14 ± 0.02 | 31 | 0.997 | 984.27 ± 94.54 |
| 3 | 0.08 ± 0.02 | 31 | 0.998 | 1092.88 ± 107.40 |
| 4 (moderate exercise) | 0.16 ± 0.02 | 41 | 0.995 | 578.36 ± 44.56 |
| 5a (rest) | 0.09 ± 0.02 | 31 | 0.996 | 1219.29 ± 73.98 |
| 5b (heavy exercise) | 0.47 ± 0.03 | 20 | 0.995 | 289.60 ± 106.60 |
| 6 | 0.164 ± 0.005 | 100 | 0.999 | 858.87 ± 191.94 |
| 7 | 0.148 ± 0.005 | 100 | 0.999 | 741.47 ± 87.55 |
| 8 | 0.156 ± 0.003 | 100 | 0.999 | 913.69 ± 129.84 |

Figure 4:
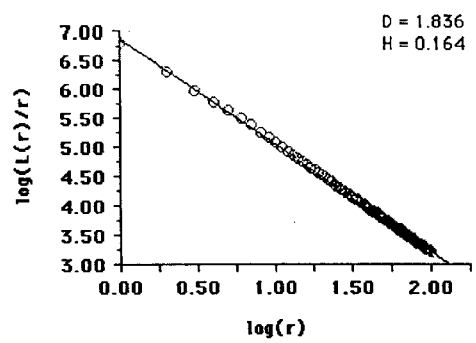
FIG. 4 illustrates a log (r) v. log [L(r)/r] plot for the IBI time series taken from subject 6 in Table 1.

FIG. 4 illustrates a plot of log (r) vs. log [L(r)/r] calculated from a set of 98,355 IBI data points obtained from subject 6 with embedding dimension n=3 and scales M=100. The linear slope of the plot suggests that a power-law relationship is present, supporting the assumption of self-similarity of the IBI time series for the range of scales investigated. Similar analyses of data sets from the other subjects resulted in qualitatively similar straight line plots of log (r) vs. log [L(r)/r].

The invention was also tested using synthesized IBI time series data. The synthetic IBI time series were computed using a spectral synthesis method (1) from the TSAS 3.01.1b, and were compiled and run on a DEC 3000/600S AXP.

Figure 5:
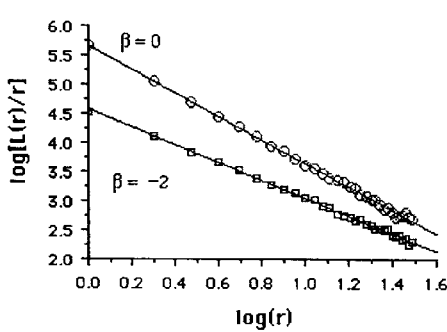
FIG. 5 illustrates a log (r) v. log [L(r)/r] plot for a computer-generated IBI times series.

The invention was tested using a computer-generated IBI time series with mean IBI=1000 ms, standard deviation SD=200, and data length N=1000. The spectral slope in the synthesis was set to two values: 0 and 2. L(r) was determined using equation (3) with an embedding dimension of n=3 and a scale of M=31, and D was determine using equation (4). FIG. 5 illustrates the log (r) vs. log [L(r)/r] plot for the two synthesized IBI time series with the same means and standard deviations but differing spectral slopes. The circles and squares represent points determined from time series generated using the spectral synthesis method with β=0 and β=−2, respectively, where β refers to the spectral slope in the generating function. Respective values for D and its standard error for regression are 2.01±0.02 and 1.53±0.01. FIG. 5 illustrates that the approximate expected results are obtained for D=2 and H=0 for the time series with a spectral slope β=0, and for D=1.5 and H=0.5 for the time series with a spectral slope β=−2.

The determination of H by the invention was tested by varying the statistical moments of the time series while holding the spectral noise characteristics steady. Several time series of data length N=1000 were generated, and the statistical moments were varied while maintaining the spectral slope at 0 or 2. Further, D was calculated using a scale of M=31, and an embedding dimension of n=3. In Table 2, the first and second columns list the mean and standard deviation, respectively, in milliseconds for IBI, the third column lists the coefficient of variation (CV), the fourth column lists computed values of H when H=0, and the fifth column lists computed values of H when H=0.5.

TABLE 2

Effect of signal characteristics on computed H-values

| Mean IBI (ms) | SD (ms) | CV | H = 0 | H = 0.5 |
|---|---|---|---|---|
| 1034.33 | 91.32 | 0.088 | 0.00 | 0.47 |
| 834.33 | 73.66 | 0.088 | 0.00 | 0.47 |
| 634.33 | 56.01 | 0.088 | 0.00 | 0.45 |
| 1034.33 | 182.65 | 0.177 | 0.00 | 0.42 |
| 1034.33 | 365.30 | 0.354 | 0.01 | 0.45 |

In Table 2, the results show good agreement with theoretical values of H=0 for a spectral slope β=0, and H=0.5 for a spectral slope β=−2. These results suggest that the invention is insensitive to mean and standard deviation differences of the time series. For H=0.5, a bias existed in that an underestimation of the true value occurred with an embedding dimension of n=3.

To determine the effect of the embedding dimension n on the invention, the embedding dimension n was varied, and H was calculated. The results are shown in Table 3. In Table 3, the first column lists the six embedding dimensions used, the second column lists H and its standard error (H±SEM) for a synthesized time series with a spectral slope of β=0 and an expected H=0, the third column lists H and its standard error (H±SEM) for a synthesized time series with a spectral slope of β=2 and an expected H=0.5, and the fourth column lists H and its standard error (H±SEM) for a human subject. The second, third, and fourth columns in Table 3 were calculated for N=1000 IBI data points, M=31, and a mean IBI and its standard deviation of 864.29±76.39 ms.

TABLE 3

Dependence of H on Embedding Dimension

| | H ± SEM | | |
|---|---|---|---|
| Embedding Dimension n | Expected H = 0.00 | Expected H = 0.50 | Human Subject |
| 6 | 0.00 ± 0.01 | 0.49 ± 0.01 | 0.29 ± 0.03 |
| 5 | 0.00 ± 0.01 | 0.48 ± 0.01 | 0.29 ± 0.03 |
| 4 | 0.01 ± 0.01 | 0.46 ± 0.01 | 0.29 ± 0.03 |
| 3 | 0.00 ± 0.01 | 0.46 ± 0.01 | 0.29 ± 0.03 |
| 2 | 0.01 ± 0.02 | 0.45 ± 0.01 | 0.30 ± 0.03 |
| 1 | 0.02 ± 0.03 | 0.43 ± 0.02 | 0.31 ± 0.03 |

As can be seen in Table 3 for the synthetic data in the second and third columns, a higher embedding dimension is required to achieve less bias in the estimation of H. This is expected because the synthetic data has a longer "memory" and is thus closer to an ideal fractal. However, for the human subject data in the fourth column, an embedding dimension of n=3 was sufficient.

When the embedding dimension is n>1, the scaling behavior of the time series with respect to phase, as well as time, can be examined. Given the results in Table 3, it appears that the influence of the magnitude of previous IBIs on a particular IBI is exerted within 2 to 3 heartbeats, at least within the data lengths examined in the present study of up to 1197 data points. Since no human EKG data that was analyzed resulted in H>0.5, and since EKG data had values of 0.01<H<0.5, an embedding dimension of n=3 is preferably used for calculating H in human subjects.

Figure 6:
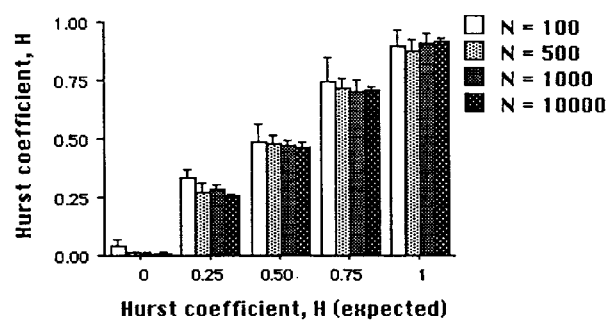
FIG. 6 illustrates the results from varying the data length using the invention.

The effects of varying data length N on the determination of H was tested by synthesizing a set of time series by varying H from 0 to 1 in increments of 0.25 with a mean of 1000 and a standard deviation of SD=200. For each value of H and N, five time series and the mean and standard deviation of the estimated value of H were determined. The embedding dimension was n=6. To avoid problems with bias inherent in the spectral synthesis method, only the initial N data points of the generated time series were used for the analysis, and the total length of the original time series was 10N. The results are shown in FIG. 6. The values represented on the y-axis show the calculated values of H, and the values of H shown on the x-axis are those used to generate the time series. The bar plots show the mean values of H for each of the time series, and the error bars represent their standard deviations.

For short series with N≧1000 points, the estimate of H obtained using the invention is more accurate than estimates obtained with other regression-based methods, including the power spectral density, discrete wavelet transform, and dispersive analysis methodologies (4), (2). With N≧500 points, H converges reasonably to the expected values determined by the generating algorithm.

Neither differences in the means and standard deviations of the signal nor variations significantly alter the estimated value of H. These strengths of the invention allow the estimation of H from relatively short data sets, such as might be obtained from 3 to 5 minutes of EKG recordings. More importantly, data sets from different subjects or different physiological states of a subject can be compared and contrasted because, by using the invention, these data sets will be relatively independent of differences in data collection time.

An important implication of the invention relates to the problem of measuring the continually changing underlying dynamics of many biologically generated time series. Since any estimation of H must, of necessity, be a time averaged value, the ability of the invention to discriminate variations in the dynamics of time series within resolutions of 100–500 data points is an advantage in the study of biological systems.

The characterization of biological signals, such as heart rate variability, can be improved by assessing the internal underlying dynamics of such time series at relatively high resolutions. Studying changes of the dynamic properties using the invention can provide insight into the generation of deterministic chaos by the interplay of oscillatory homeostatic feedback loops, as they appear to operate in the generation of IBI time series (6).

With the invention, a proper embedding dimension n must be chosen for the time series. In part, the choice of the embedding dimension is dependent on the complexity of the underlying dynamics, which may change with time. The choice is straightforward for a relatively short time series, since the embedding constant can be incrementally changed and H calculated after each increment. At some point, further increases in the embedding dimension do not appreciably change the value of H, as shown in Table 3. For a longer time series, it is possible that epochs with very complex internal dynamics might co-exist and be contiguous to epochs with low complexity. H could thus be overestimated or underestimated if an "average" embedding dimension were chosen based on the results of the whole time series. As discussed above, an embedding dimension of n=3 is preferably used for human subjects. However, as noted, minimal experimentation with a particular time series data set may result in a more optimal embedding dimension.

In the case of a synthetic time series with an "infinite" memory, the choice of a low value for the embedding dimension may result in a bias in the estimation of H. As shown in Table 3, H tended to be underestimated for time series with H close to 0.50, unless the embedding dimension was set to at least 6.

Further, with the invention, H can be calculated in real-time from a stream of input time series data, including biologically generated time series data, such as IBI time series data. This permits the immediate examination of the internal dynamics of any input time series.

Detecting Biological Conditions Using the Invention

The invention can be used to detect a variety of biological conditions. First, alcohol dependence and gender are discussed, and then other types of biological conditions are described for detection using the invention.

The inventor has discovered that determining H from IBI time series data can be used to detect biological conditions by providing a measure of cardiac signal complexity in relationship to the biological condition, such as alcohol dependence or gender. With the invention, the internal dynamics of an IBI time series are understood by determining H. Further, with the invention, a better representation of the internal dynamics of a system can be obtained than from simple dispersional measures, such as mean and standard deviation determinations. Moreover, with the invention, a special transform of the IBI data is not required prior to analysis, and short lengths of IBI data with differing statistical characteristics can be compared.

The invention can be used to determine H using IBI time series data obtained from human subjects stratified based on gender and the presence or absence of alcohol dependence. Decreases in HRV, defined as beat-to-beat variations of human heartbeat intervals, measured both in the frequency domain and the time domain, are associated with higher values of H (15). The inventor has discovered that a higher H value characterizes EKG data from alcoholic subjects as compared to controls. This discovery is supported by previous studies in this population group that have shown decreases in HRV measures in alcoholic subjects compared to non-alcoholic subjects (16).

An experimental study using the invention was approved by the Institutional Review Board at the National Institutes of Health, and was carried out with written consent from the subjects. Potential subjects were evaluated using the SADS (Schedule for Affective Disorders and Schizophrenia) and the SCID (Structured Clinical Interview for DSM-III-r) (17). Subjects were instructed not to consume any prescription or non-prescription drug for 24 hours prior to the start of testing. Urine toxicology testing was performed, and blood alcohol concentrations were estimated using a breathalyzer. Subjects who were positive for drugs of abuse or alcohol were excluded.

From the surrounding community, 120 volunteer subjects were obtained and evaluated. Two groups of subjects were abstracted from this study population. Subjects with a primary diagnosis of alcohol dependence, and no other Axis I or Axis II disorders were designated for the alcoholic group. Healthy comparison subjects without evidence of Axis I or Axis II disorders were placed in the control group. The final study group consisted of 61 subjects, 13 who met criteria for alcohol dependence (6 females and 7 males, mean age±SEM of 40.0±3.8 years), and 48 healthy comparison subjects (33 females and 15 males, mean age±SEM of 40.3±2.7 years). Racial composition of the study subjects included 48 Caucasians and 13 African-Americans, proportionally distributed across gender and alcohol groups.

Subjects were seated in a comfortable, quiet room monitored through a closed circuit video camera. On each subject, two silver-silver chloride electrodes were attached laterally, along the mid-axillary line, beneath the last rib. The electrodes were referenced to each other. Pre-testing impedance was measured at 5K ohms or below. The EKG signals were amplified via 12 A amplifiers (Grass, Quincy, Mass.) with standard amplification filters set between 0.01 and 100 Hz. Data was calibrated against an average 100 uV 5 Hz sine wave and digitized with the use of a 12-bit A-to-D converter (Data Translation, Marlboro, Mass.).

Subjects were asked to minimize movement while EKG data was recorded for approximately 7 minutes. For the first approximately 3.5 minutes of data collection, the subject was asked to keep his or her eyes open. For the second approximately 3.5 minutes of data collection, the subject was asked to keep his or her eyes closed.

Data was analyzed in blind fashion, both during the EKG filtering process, as well as during the determination of H. The code relating the subjects and the results was broken after all data was processed and ready for statistical analysis.

The digitized EKG data was mathematically filtered with a band pass filter to reduce noise-to-signal ratio. A computer program, written in C (Borland, Scotts Valley, Calif.) was used to extract the IBIs from the data set. The IBIs were then manually checked for anomalies. The criteria for the admissibility for anomalies in the EKG data was extremely stringent. Corrections were made only if the irregular IBI differed from the mean IBI by a factor of 2. Abnormal beat-to-beat intervals were corrected by removing beats, depending on the situation. Out of the 61 subjects, each with approximately 200 data points per condition, only four anomalous readings were removed.

Using the invention, the IBI time series data was processed, as previously discussed with FIG. 1, with an embedding dimension of n=3 and a maximum value of r as M=10. Linear regression, using a least mean square fit of the log (r) vs. log [L(r)/r]plot was performed, and the slope of −D was used to derive H according to the relationship in equation (3). For all linear regressions, $R^2 \geq 0.98$.

The value of H was compared and contrasted for the alcoholic and control groups using a two-factor (alcohol status and gender) parametric analysis of variance (ANOVA) for each condition (eyes open or eyes closed). Using the parameters derived from the ANOVA, group means were explored for significant differences using a Bonferroni/Dunn correction. The significance level was set to p>0.05.

Upon examining the experimental results, there were no significant differences in mean IBI between the two groups under each experimental condition, as shown in Table 4 below. In Table 4, the first column lists the two groups, the second column lists the two experimental conditions, the third column lists the count for the number of subjects, and the fourth and fifth columns list the mean IBI and the standard deviation (SD) in milliseconds, respectively.

TABLE 4

Mean IBI ± Standard Deviation by Group and Condition

| Group | Condition | Count | Mean IBI (ms) | SD |
|---|---|---|---|---|
| Alcoholic | Open Eyes | 13 | 922.60 | 153.52 |
| Alcoholic | Closed Eyes | 13 | 946.57 | 143.52 |
| Control | Open Eyes | 48 | 939.62 | 133.39 |
| Control | Closed Eyes | 48 | 949.83 | 132.00 |

Figure 7:
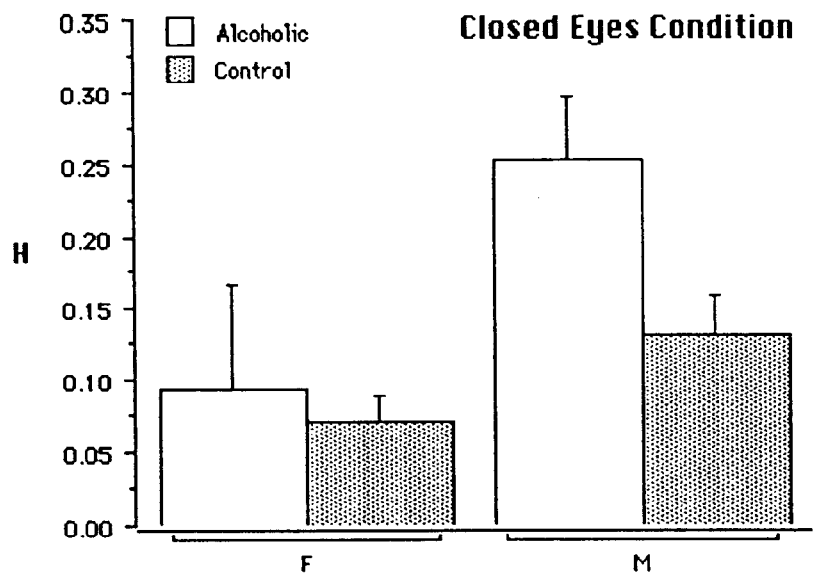
FIG. 7 illustrates the experimental results obtained from determining the Hurst exponent for human subjects with their eyes closed.
Figure 8:
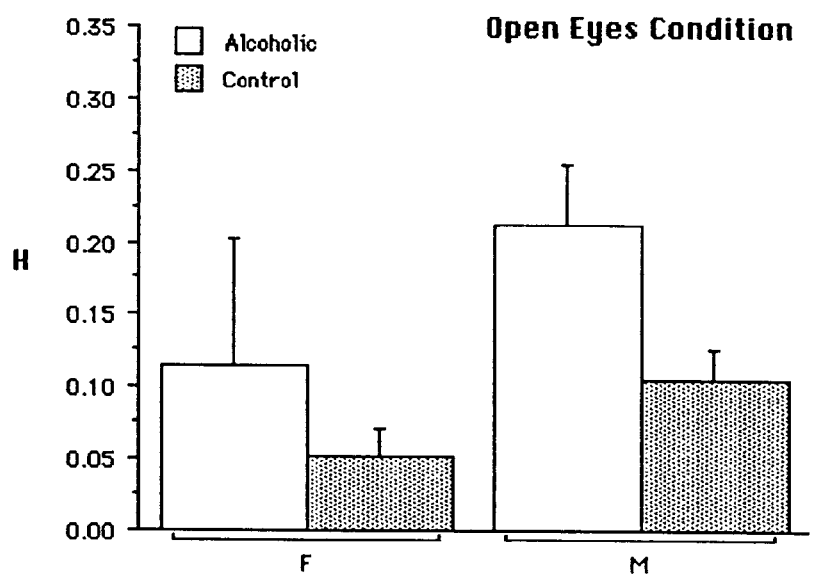
FIG. 8 illustrates the experimental results obtained from determining the Hurst exponent for human subjects with their eyes open.

As shown in FIGS. 7 and 8, both alcohol use and male gender are correlated with higher values of H. In FIG. 7, the values of H obtained in the closed eyes condition are plotted by group, alcoholic vs. control, as indicated in the legend and segregated by gender: women (F) and men (M). The error bars above the columns represent the standard error (SEM). In FIG. 8, the values of H obtained in the open eyes condition are plotted by group, alcoholic vs. control, as indicated in the legend and segregated by gender: women (F) and men (M). The error bars above the columns represent SEM.

Table 5 lists the values of H and its standard error (H±SEM) obtained from each sub-group under the two experimental conditions in the experimental study.

TABLE 5

H ± SEM

| | Alcoholic | | | Control | | |
|---|---|---|---|---|---|---|
| Condition | Female (n = 6) | Male (n = 7) | All (n = 13) | Female (n = 33) | Male (n = 15) | All (n = 48) |
| Closed Eyes | 0.09 ± 0.07 | 0.25 ± 0.04 | 0.18 ± 0.05 | 0.07 ± 0.02 | 0.13 ± 0.03 | 0.09 ± 0.02 |
| Open Eyes | 0.12 ± 0.09 | 0.21 ± 0.04 | 0.17 ± 0.05 | 0.05 ± 0.02 | 0.11 ± 0.02 | 0.07 ± 0.02 |

Table 6 lists the parameters for the experimental study derived from the ANOVA.

TABLE 6

ANOVA Results

| | Conditions | |
|---|---|---|
| Effects | Closed Eyes | Open Eyes |
| Alcohol vs. Control | $p \leq 0.014$ | $p \leq 0.011$ |
| Male vs. Female | $p \leq 0.003$ | $p \leq 0.018$ |

Sub-group analysis shows that for males, alcohol use is associated with an increase in H ($p \leq 0.05$) under both experimental conditions. Further, H values from females in the alcoholic group do not differ significantly from H values from females in the control group. However, given the low number of subjects in the alcoholic group and the high dispersion of H, the probability of a Type II error is high.

The experimental results extend previous observations that heart rhythms of healthy subjects generate IBI time series with H close to 0. The value of H for all healthy control subjects in the open eye condition was 0.07±0.11 (mean±SD). This value compares with H=0.083±0.139 calculated using CGSA with a sample of 5 healthy subjects and 512 data points (19). Although significant differences in H between the closed eyes condition and open eyes condition were not observed, a trend appears as a slightly lower H in the closed eyes condition as compared to the open-eyes condition in the control group. This would be expected if oculomotor and vestibular activities are associated with inhibition of the vagally mediated baroreflex control of heart rate (19).

Further, the experimental results using the invention to determine H confirm previous observations that women appear to have more complex heart-rate dynamics than men. Instead of using H, the previous studies used an approximate entropy measure (20).

The experimental results strongly suggest that chronic excessive alcohol use results in simplification of cardiac heart rate dynamics, as determined by a measure of auto-correlation, namely H. In particular, alcoholic subjects show increased values of H compared to non-alcoholic subjects. This decreased level of auto-correlation is associated with decreased signal complexity. Particular inherited traits, which might be associated with pre-morbid alterations in HRV, might increase the risk of developing alcohol dependence. It is also possible that alcohol use partially or completely determined the observed changes in heart rate dynamics as a consequence of effects on the autonomic nervous system.

The presence of alcohol withdrawal syndrome (AWS) in the alcoholic subjects, and its consequent disruption of autonomic equilibrium, might partially account for the experimental results. Alcoholic subjects were studied more than 24 hours from their last alcohol consumption, by self-report, and were determined to be alcohol free at the time of the study. The lack of significant differences in heart rate between the alcoholic and control groups suggests that if AWS was occurring at the time of the study, its effects on the sympathetic nervous system were not significant enough to be reflected by relative tachycardia. Nevertheless, sub-clinical AWS might have altered the reflex regulation of heart rate, perhaps by increasing sympathetic nervous system activity. This might result in a decrease in auto-correlation and contribute to an elevation of H.

One explanation for the decreased HRV in alcoholics is decreased parasympathetic nervous system (PNS) modulation of the heart rate. However, the finding of lower HRV would not necessarily imply a decrease in PNS activity because, although PNS blockade decreases measures of HRV, decreases in PNS activity are not associated with changes of HRV in the absence of central nervous system (CNS) input and modulation (21). These data, taken together, suggest that an abnormality in central and peripheral feedback regulation of heart rate may be present in alcoholic subjects. The dysregulation may be sufficient, even in the absence of changes in PNS activity, to result in measurable changes in HRV parameters. This dysregulation could be due to either a pre-existing trait, as a result of chronic excessive alcohol consumption, or an interaction between these two factors.

In addition to detecting alcoholism in human subjects, the invention can also be used to detect other biological conditions in biological subjects that are manifested as a change in H.

For example, the invention can be used to detect changes in serotonin in a biological subject, such as a human. Serotonin is a key neurochemical effector of both central and peripheral modulation of PNS activity. Acting via 5-HT3 receptors present on vagal fibers, peripherally administered 5-HT3 receptor agonists stimulate acetylcholine release inducing bradycardia (22). Centrally administered, these same agents decrease peripheral acetylcholine release via inhibitory 5HT3 receptors present in the nucleus tractus solitarius (23). Evidence of decreased central 5HT3 receptor function has been found in rats consuming alcohol on a chronic basis (24). Low serotonin turnover is positively correlated with Type II alcoholism (25), while chronic excessive alcohol consumption appears to decrease serotonergic function (26). Taken together, these data suggest that decreases in both 5-HT3-receptor sensitivity and in serotonergic turnover might contribute to decreases in HRV seen in alcoholics. Additionally, HRV studies in women show elevations in the high-frequency spectral power associated with PNS activation compared to males, while estrogens are known to strongly increase serotonin turnover (20, 27, 28). Furthermore, treatment of psychiatric disorders with selective serotonin reuptake inhibitors, which also increase serotonin turnover, results in similar increases in HRV (29).

Both autonomic neuropathy and cardiomyopathy have been shown to result in decreases in HRV and simplification of cardiac dynamics. These conditions are relatively common in alcoholics (30, 31, 32). Decreased cardiac complexity has been found to be predictive of ventricular tachycardia after myocardial infarction and in patients with coronary artery disease (33, 34). Since increased cardiovascular mortality in alcoholics is known to be associated with the degree of autonomic neuropathy, measures of HRV can be used in predicting end-organ damage and future cardiovascular mortality in an alcoholic population.

Further, the invention can be used to detect other biological conditions, such as a psychiatric disorder. Dysregulation of the serotonergic axis is associated with certain psychiatric disorders which have also been shown to result in alterations in HRV measures. Examples include major depression (35), generalized anxiety disorder (36), post-traumatic stress disorder (37), and panic disorder (38). Because the invention is sensitive to perturbations of HRV, changes in H determined from EKG data can be associated with these and other psychiatric disorders which involve disruption of the serotonergic axis.

Moreover, the invention can be used to detect other biological conditions associated with the heart, such as cardiac arrhythmia, coronary disease, autonomic neuropathy, and cardiomyopathy. Alteration of HRV has been shown to be predictive of cardiac arrhythmias (39, 40, 41, 42) and coronary artery disease (43). Further, alterations in HRV, reflected by changes in the H determined from EKG data, can be used to assess the risk factors for cardiac arrhythmias, both as a result of cardiovascular disease processes, as well as adverse effects of drugs which alter HRV (44).

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A method using a computer for determining statistical information for time series data for a measurable activity, the method comprising the steps of:
    obtaining the time series data of the measurable activity, the time of the series data comprising a plurality of data elements representative of the measurable activity; and
    using a computer to determine a Hurst exponent from the time series data, the Hurst exponent being the statistical information of the time series data.

2. A method according to claim 1, wherein the step of determining the Hurst exponent comprises the step of:
    determining a plurality of lengths L(r) for a plurality of sampling resolutions r for a plurality of self-similar fractal curves for the time series data.

3. A method according to claim 2, wherein the length L(r) and the sampling resolution r are related by:

$$L(r) = \sum_{i=0}^{I}\left[\sum_{k=0}^{n-1}(S_{ir+k} - S_{ir+r+k})^2\right]$$

where the plurality of data elements of the time series data are represented by $S_1, S_2, S_3, \ldots, S_N$, r=1,2,3, ..., M, I is the integer part of (N-r-n+1)/r, and n≧1 is an embedding dimension.

4. A method according to claim 2, wherein the step of determining the Hurst exponent further comprises the step of:
determining a linear relationship between log (r) and log [L(r)/r].

5. A method according to claim 4, wherein the step of determining the Hurst exponent further comprises the step of:
determining a slope of the linear relationship between log (r) and log [L(r)/r].

6. A method according to claim 5, wherein the step of determining the Hurst exponent further comprises the step of:
determining the Hurst exponent from the slope of the linear relationship between log (r) and log [L(r)/r].

7. A method according to claim 1, wherein obtaining the time series data comprises measuring the measurable activity to obtain the time series data.

8. A method according to claim 1, wherein obtaining the time series data comprises retrieving the time series data from a computer-readable medium.

9. A method according to claim 1, wherein the measurable activity is a biologically generated activity.

10. A method according to claim 1, wherein the time series data are representative of measurements of heart rate variability.

11. A method according to claim 1, further comprising the step of:
detecting a biological condition using the Hurst exponent.

12. A method according to claim 11, wherein the biological condition is alcoholism.

13. A method according to claim 11, wherein the biological condition is related to a change in serotonin activity in a biological subject.

14. A method according to claim 11, wherein the biological condition is related to the heart of a biological subject.

15. A method according to claim 11, wherein the biological condition is a psychiatric disorder.

16. An apparatus for determining statistical information for time series data for a measurable activity, comprising:
means for obtaining the time series data of the measurable activity, the time series data comprising a plurality of data elements representative of the measurable activity; and
means for determining a Hurst exponent from the time series data, the Hurst exponent being the statistical information of the time series data.

17. An apparatus according to claim 16, wherein said means for determining the Hurst exponent comprises:
means for determining a plurality of lengths L(r) for a plurality of sampling resolutions r for a plurality of self-similar fractal curves for the time series data.

18. An apparatus according to claim 17, wherein the length L(r) and the sampling resolution r are related by:

$$L(r) = \sum_{i=0}^{I}\left[\sum_{k=0}^{n-1}(S_{ir+k} - S_{ir+r+k})^2\right]^{1/2}$$

where the plurality of data elements of the time series data are represented by $S_1, S_2, S_3, \ldots, S_N$, r=1,2,3, ..., M, I is the integer part of (N-r-n+1)/r, and n≧1 is an embedding dimension.

19. An apparatus according to claim 17, wherein said means for determining the Hurst exponent further comprises:
means for determining a linear relationship between log (r) and log [L(r)/r].

20. An apparatus according to claim 19, wherein said means for determining the Hurst exponent further comprises:
means for determining a slope of the linear relationship between log (r) and log [L(r)/r].

21. An apparatus according to claim 20, wherein said means for determining the Hurst exponent further comprises:
means for determining the Hurst exponent from the slope of the linear relationship between log (r) and log [L(r)/r].

22. An apparatus according to claim 16, wherein said means for obtaining the time series data comprises means for measuring the measurable activity to obtain the time series data.

23. An apparatus according to claim 16, wherein said means for obtaining the time series data comprises means for retrieving the time series data from a computer-readable medium.

24. An apparatus according to claim 16, wherein the measurable activity is a biologically generated activity.

25. An apparatus according to claim 16, wherein the time series data are representative of measurements of heart rate variability.

26. An apparatus according to claim 16, further comprising:
means for detecting a biological condition using the Hurst exponent.

27. An apparatus according to claim 26, wherein the biological condition is alcoholism.

28. An apparatus according to claim 26, wherein the biological condition is related to a change in serotonin activity in a biological subject.

29. An apparatus according to claim 26, wherein the biological condition is related to the heart of a biological subject.

30. An apparatus according to claim 26, wherein the biological condition is a psychiatric disorder.

31. A computer-readable medium embodying code segments for determining statistical information for time series data for a measurable activity, comprising:
code segments for obtaining the time series data of the measurable activity, the time series data comprising a plurality of data elements representative of the measurable activity; and
code segments for determining a Hurst exponent from the time series data, the Hurst exponent being the statistical information of the time series data.

32. A computer-readable medium according to claim 31, wherein said code segments for determining the Hurst exponent comprise:
code segments for determining a plurality of lengths L(r) for a plurality of sampling resolutions r for a plurality of self-similar fractal curves for the time series data.

33. A computer-readable medium according to claim 32, wherein the length L(r) and the sampling resolution r are related by:

$$L(r) = \sum_{i=0}^{I} \left[ \sum_{k=0}^{n-1} (S_{ir+k} - S_{ir+r+k})^2 \right]^{1/2}$$

where the plurality of data elements of the time series data are represented by $S_1, S_2, S_3, \ldots, S_N$, $r=1,2,3, \ldots, M$, I is the integer part of $(N-r-n+1)/r$, and $n \geq 1$ is an embedding dimension.

34. A computer-readable medium according to claim 32, wherein said code segments for determining the Hurst exponent further comprise:
  code segments for determining a linear relationship between log (r) and log [L(r)/r].

35. A computer-readable medium according to claim 34, wherein said code segments for determining the Hurst exponent further comprise:
  code segments for determining a slope of the linear relationship between log (r) and log [L(r)/r].

36. A computer-readable medium according to claim 35, wherein said code segments for determining the Hurst exponent further comprise:
  code segments for determining the Hurst exponent from the slope of the linear relationship between log (r) and log [L(r)/r].

37. A computer-readable medium according to claim 31, wherein said code segments for obtaining the time series data comprise code segments for measuring the measurable activity to obtain the time series data.

38. A computer-readable medium according to claim 31, wherein said code segments for obtaining the time series data comprise code segments for retrieving the time series data from a computer-readable medium.

39. A computer-readable medium according to claim 31, wherein the measurable activity is a biologically generated activity.

40. A computer-readable medium according to claim 31, wherein the time series data are representative of measurements of heart rate variability.

41. A computer-readable medium according to claim 31, further comprising:
  code segments for detecting a biological condition using the Hurst exponent.

42. A computer-readable medium according to claim 41, wherein the biological condition is alcoholism.

43. A computer-readable medium according to claim 41, wherein the biological condition is related to a change in serotonin activity in a biological subject.

44. A computer-readable medium according to claim 41, wherein the biological condition is related to the heart of a biological subject.

45. A computer-readable medium according to claim 41, wherein the biological condition is a psychiatric disorder.

* * * * *